(12) United States Patent
Widulle

(10) Patent No.: US 10,105,304 B2
(45) Date of Patent: Oct. 23, 2018

(54) SKIN PROTECTOR

(71) Applicant: COR S.A.R.L., Luxembourg (LU)

(72) Inventor: Herbert Widulle, Hamburg (DE)

(73) Assignee: COR S.A.R.L., Luxembourg (LU)

( * ) Notice: Subject to any disclaimer, the term of this patent is extended or adjusted under 35 U.S.C. 154(b) by 0 days.

(21) Appl. No.: 15/112,983

(22) PCT Filed: Dec. 29, 2014

(86) PCT No.: PCT/EP2014/079366
§ 371 (c)(1),
(2) Date: Jul. 20, 2016

(87) PCT Pub. No.: WO2015/106945
PCT Pub. Date: Jul. 23, 2015

(65) Prior Publication Data
US 2016/0374917 A1 Dec. 29, 2016

(30) Foreign Application Priority Data
Jan. 20, 2014 (EP) ..................................... 14151751

(51) Int. Cl.
| A61K 8/58 | (2006.01) |
| A61K 8/86 | (2006.01) |
| A61K 8/892 | (2006.01) |
| A61K 8/37 | (2006.01) |
| A61K 8/92 | (2006.01) |
| A61K 8/891 | (2006.01) |
| A61K 8/81 | (2006.01) |
| A61Q 19/00 | (2006.01) |
| A61Q 17/00 | (2006.01) |

(52) U.S. Cl.
CPC ............... *A61K 8/585* (2013.01); *A61K 8/37* (2013.01); *A61K 8/8152* (2013.01); *A61K 8/86* (2013.01); *A61K 8/891* (2013.01); *A61K 8/892* (2013.01); *A61K 8/922* (2013.01); *A61Q 17/00* (2013.01); *A61Q 19/00* (2013.01); *A61K 2800/31* (2013.01); *A61K 2800/95* (2013.01)

(58) Field of Classification Search
None
See application file for complete search history.

(56) References Cited

U.S. PATENT DOCUMENTS

| 7,416,735 B2 * | 8/2008 | El-Nokaly | A61K 8/0241 424/400 |
| 2004/0081679 A1 | 4/2004 | Simon et al. | |
| 2005/0112072 A1 * | 5/2005 | Wang | A61K 8/042 424/63 |
| 2005/0265943 A1 | 12/2005 | Geffroy-Hyland | |
| 2006/0039885 A1 * | 2/2006 | Nishio | A61K 8/0208 424/70.122 |
| 2006/0110346 A1 * | 5/2006 | Lu | A61K 8/31 424/64 |
| 2008/0051497 A1 * | 2/2008 | Lu | A61K 8/042 524/394 |
| 2010/0297050 A1 * | 11/2010 | Bui | A61K 8/31 424/64 |
| 2012/0171266 A1 | 7/2012 | Cantwell | |
| 2013/0022643 A1 | 1/2013 | Sternoff et al. | |

FOREIGN PATENT DOCUMENTS

| DE | 102006003069 A1 | 7/2007 |
| EP | 1405634 A1 | 4/2004 |
| EP | 1774951 A1 | 4/2007 |
| EP | 1854450 A2 | 11/2007 |
| EP | 1927344 A1 | 6/2008 |
| EP | 2896429 A1 | 7/2015 |
| KR | 2009-0056300 | 6/2009 |
| KR | 2009-0056300 A | 6/2009 |
| TW | 200900092 | 1/2009 |
| WO | WO 92/19215 A1 | 11/1992 |
| WO | WO 2002/003950 A2 | 1/2002 |
| WO | WO 2003/004070 A1 | 1/2003 |
| WO | WO 2007/132273 A2 | 11/2007 |
| WO | WO 2010/135736 | 11/2010 |
| WO | WO 2012/098116 A1 | 7/2012 |
| WO | WO 2013/131107 | 9/2013 |
| WO | WO 2015/106945 A1 | 7/2015 |

OTHER PUBLICATIONS

Silform flexible resin, 2009-2011, pp. 1-12 ([retrieved on-line website: https://www.momentive.com/WorkArea/DownloadAssetaspx?id=24834, last visit Jan. 19, 2017]).*
Naveed Akhtar et al., "Rheological Studies and Characterization of Different Oils", Journal of the Chemical Society of Pakistan, vol. 31, No. 2, 2009, 201-206.
"Pluriol® P 2000 Polypropylene Glycol", Technical Bulletin, BASF The Chemical Company (2011).
Brookfield Dial Viscometer, Operating Instructions, Manual No. M/85-150-P700, accessed on Aug. 12, 2016.
Chemsil Silicones, Inc., Product Information Sheet for Cosmetic fluid 7007-DM (Feb. 2013).
ExxonMobil Chemical Synthetics Division, Chemistries for Personal Care, PureSyn™ Polyalphaolefins (PAO), (Accessed on Aug. 12, 2016).
Kraton Datasheet, Kraton® G1657 M Polymer (Oct. 2, 2012).
Momentive Marketing Bulletin, "Silform* Flexible Resin, Specialty Fluids—Personal Care", (Feb. 2011).

(Continued)

*Primary Examiner* — Ernst V Arnold
*Assistant Examiner* — Kyung S Chang
(74) *Attorney, Agent, or Firm* — Knobbe, Martens, Olson & Bear, LLP

(57) ABSTRACT

The invention relates to an oil-based skin protector for application to the human skin comprising at least one film former as well as the use thereof.

13 Claims, No Drawings

(56) References Cited

OTHER PUBLICATIONS

Office Action issued in European Application No. 14151751.6 dated Apr. 14, 2016.
Office Action issued in European Application No. 14151751.6 dated Jul. 9, 2015.
Pinnagoda et al., "Guidelines for Transepidermal Water Loss (TEWL) Measurement", http://onlinelibrary.wiley.com/doi/10.1111/06000536.1990.tb01553.x/abstract, (1990).
Response to Office Action issued in European Application No. 14151751.6 (dated Jan. 11, 2016).
Extended European Search Report for EP 14157151.6 dated Jun. 10, 2014.
Response to Extended European Search Report dated Oct. 23, 2014.
International Preliminary Report on Patentability in Application No. PCT/EP2014/079366 dated Apr. 2, 2015.
Van Reeth et al., "New Silicone Resin Film Formers for Longer Wear and Enhanced Comfort", dowcorning.com/personal care (accessed on Aug. 12, 2016).
Wacker Silicones, BELSIL® DM 300000, Dimethicone, Technical data sheet for BELSIL® DM 300000 / Version: 1.2 / Date of last alteration: Mar. 17, 2011; English Version.
Wacker Silicones, BELSIL® DM 300000, Dimethicone, Technical data sheet for BELSIL® DM 300000 / Version: 1.3 / Date of last alteration: Jun. 7, 2013; German Version.
BELSIL DM 300000 product information (last altered Mar. 2011)—changes appearing in German version of Jun. 2013.
Wacker Silicones, BELSIL® DM 3096, Dimethicone, Dimethiconol, Technical data sheet for BELSIL® DM 3096 / Version: 1.1 / (Date of last alteration: Nov. 30, 2011).
International Search Report and Written Opinion issued in application No. PCT/EP2014/079366 dated Apr. 2, 2015.
European Office Action issued in application No. 14151751.6 dated Nov. 15, 2016.
Technical data sheet for SILRES® MK / Version: 1.5 / Methyl Silicone Resin, Jun. 11, 2014.
Technical data sheet for Momentive / Tospearl 2000B, Mar. 13, 2018.

* cited by examiner

SKIN PROTECTOR

This application is the U.S. National Phase under 35 U.S.C. § 371 of International Application No. PCT/EP2014/079366, filed Dec. 29, 2014, designating the U.S., and published in English as WO 2015/106945 A1 on Jul. 23, 2015, which claims priority to European Patent Application No. 14151751.6, filed Jan. 20, 2014, the entire contents of which are incorporated herein by reference.

BACKGROUND OF THE INVENTION

Field of the Invention

The invention relates to an oil-based skin protector for application to the human skin comprising at least one film former as well as the use thereof.

Description of Related Art

Some cosmetic compositions are known in the prior art.

KR20090056300 describes a cosmetic composition comprising polar oil and a film former. This composition is hydrophilic and will therefore accelerate the detachment of the callused skin from the remaining skin.

EP1854450 describes a cosmetic composition comprising volatile oil and a film former.

US2012171266 describes a cosmetic composition comprising oil and a film former and solid pigments.

WO2007132273 describes a cosmetic composition comprising oil and a film former and a surfactant.

TW200900092 describes a cosmetic composition comprising mineral oil and a film former.

WO9219215 describes a cosmetic waterproofing composition comprising about 5-85% of a volatile mineral spirit.

None of these compositions seem to be suitable as a water permeable composition for the human skin, since they close the pores of the skin—either with pigments or other ingredients.

Some lubricants for the human skin are known in the prior art (for example products such as Bodyglide®).

Typically, these lubricants are based on wax or solid grease compositions. These lubricants form a solid and closed seal on the skin and act as water vapor barriers. These barriers result in building water vapor pressure upon transpiration of the human and this in turn will result in loosening of the outer cell layers of the skin. By using these lubricants, the natural heat balance of the body will be negatively affected and the outer protective layer of the skin will be removed.

SUMMARY OF THE INVENTION

The problem according to the invention is to provide a long-lasting skin protector composition for the human skin that provides good permeability to water.

The problem according to the present invention is solved by an oil-based skin protector for application to the human skin comprising at least one film former.

The major advantage of the present invention is the high permeability to water. Water will not gather under the film and will not loosen the outer cell layers as described above. This way, the uppermost layer of dead callused skin is not abraded easily. The film former ensures the elasticity of the skin and protects the skin from microwounds or microfissures. The film former will fix the components of the skin protector to the skin thus prolonging the positive effect.

The term "skin protector" according to the present invention is defined as a composition that is capable of effectively protecting the skin from damage due to friction.

DETAILED DESCRIPTION

Preferably, the oil component is comprised in an amount from 45 to 70 wt. %, in particular 50 to 65 wt. %.

The oil component preferably comprises one or more compounds selected from the group consisting of squalan, neutral oil, babassu oil, coconut oil, palm kernel oil, octyl octanoate, isopropyl palmitate, isopropyl myristate, cyclopentasiloxane, cyclohexasiloxane, C12-C18 alkyl benzoate, or dodecamethylcyclohexasiloxan.

Preferably, the oil component comprises one high-molecular oil and one low-molecular oil. The high-molecular oil can be polymeric.

The oil component may also preferably comprise a volatile component. The heat of evaporation for this volatile component may be at most 60 kJ/mol. The vapor pressure for this volatile component may be at least 30 Pa at 25° C. The advantage of a volatile component also surprisingly consist of an increased glide effect on the skin after application of the skin protector.

Preferably, the transepidermal water loss (TEWL) is at least 2 g/hm$^2$, more preferably at least 6 g/hm$^2$, and most preferably at least 11 g/hm$^2$, where in all cases 0.0036 g/cm$^2$ of the skin protector were applied to the skin. TEWL values are used as an indicator of water loss from the skin. Transepidermal water loss can be measured after application of the skin protector to the skin using the method as laid out in Pinnagoda, J., et al. "Guidelines for transepidermal water loss (TEWL) measurement." *Contact dermatitis* 22.3 (1990): 164-178.

Preferably, the at least one film former is selected from the group consisting of polymethylsilsesquioxane, derivatives of polymethacrylic acid, polymethycrylic acid isobutylester, polymers comprising methylsilsesquioxy- and trialkylsilylunits, trimethylsiloxysilicate, polypropylsilsesquioxane, acrylate copolymer, acrylates/acrylamide copolymer, butyl ester of PVM/MA copolymer (copolymer of methyl vinyl ether and maleic anhydride), carboxymethyl chitin, chitosan, hydroxypropyl cellulose, polyquaternium-36, PVP (polyvinylpyrrolidone), PVP/VA (polyvinylpyrrolidone/vinyl acetate) copolymer, VA/crotonates copolymer (vinyl acetate/crotonic acid copolymer), vinyl caprolactam/PCP/dymethylaminoctyl methyacrylate copolymer, or mixtures thereof Preferably, the at least one film former is comprised in an amount from 1 to 20 wt. %, most preferably 3 to 15 wt. %, most preferably 4 to 12 wt. %.

Preferably, the film former is a solid at room temperature.

Preferably, the skin protector also comprises at least one glide agent, in particular at least one or several glide agent selected from the group consisting of polyalkylene glycol (and in particular polypropylene glycol), dimethicone, dimethiconol, jojoba oil, *butyrospermum parii*, rape seed oil.

Preferably, the glide agent is composed of at least a low-melting component and a high-melting component. The low-melting component has a melting point up to 25° C. The high-melting component has a melting point of at least 37° C. Surprisingly, this composition increased the glide effect.

Preferably, the glide agent is composed of a dimethicone with high viscosity and a dimethicone with low viscosity. The dimethicone with high viscosity may preferably have a viscosity of more than 10.000 mPa·s, whereas the dimethicone with high viscosity may preferably have a viscosity of at most 10.000 mPa·s. Alternatively, the dimethicone with high viscosity may preferably have a viscosity of more than 1.000 mPa·s.

Preferably, the glide agent is comprised in an amount from 15 to 52 wt. %, in particular 23 to 46 wt. %.

Preferably, the viscosity of the skin protector is in a range of from 10 to 10.000 mPa·s, such as a range of from 100 to 1000 mPa·s, in particular in a range of from 100 to 800 mPa·s.

Viscosity can be measured at 20° C. and 1 atmosphere. A Brookfield LVF viscosimeter can be used. The shear rate can be 0.34 N/s. Further appropriate parameters can be found in Manual No. M/85-150-P700 of Brookfield Engineering Laboratories, Inc.

Advantageously, the content of solids in the skin protector is less than 1 wt. %, in particular, less than 0.1 wt. %. The skin protector according to the invention preferably comprises less than 1 wt. % solid particles, in particular less than 0.1 wt. % solid particles, most preferably no solid particles. This way, the skin will not be irritated as much when other skin or clothing or any other sporting equipment is constantly rubbing against the skin. Sun screens typically comprise solid particles such as titanium dioxide particles. Compositions like sun screens are therefore not preferable.

Preferably, the alcohol content in the skin protector according to the invention is less than 0.5 wt. %.

Preferably, the water content in the skin protector according to the invention is less than 1 wt. %, in particular less than 0.5 wt. %. Most preferably, water is not present in the skin protector.

Preferably, the surfactant content in the skin protector according to the invention is less than 1 wt. %, in particular less than 0.5 wt. %. Most preferably, a surfactant is not present in the skin protector.

Preferably, the skin protector according to the present invention also comprises dimethylsiloxane. Surprisingly, due to this ingredient the friction with clothing or other parts of the skin was reduced significantly.

Preferably, the skin protector according to the present invention is hydrophobic. More preferably, the water contact angle of water against air at 25° C. and 1 atm is at least 90° after application of 0.0036 g/cm² skin protector to the skin.

In a further embodiment, the problem of the present invention is solved by the use of the skin protector according to the present invention for application to the human skin, in particular to the feet, under the female breast, to the upper arms, inner thighs, to the shoulders and/or to the back. Using the skin protector for this, it may prevent heat accumulation of the body. Therefore, it can even be applied to large parts of the bodies of extreme athletes such as marathon runners (e.g. half of the upper body) to alleviate or even prevent skin abrasion normally caused by functional clothing.

The features disclosed in the claims and the description can be important to the invention either by themselves or in combination with any other disclosed features.

Example 1

A skin protector with the following composition was made using the typical techniques used in the field of cosmetics:

| Compound Name (Composition 1) | Content (wt. %) |
|---|---|
| Cyclopentasiloxane (oil component) | 60 |
| Dimethicone (glide agent) | 31 |

-continued

| Compound Name (Composition 1) | Content (wt. %) |
|---|---|
| Dimethiconol (glide agent) | 4 |
| Polymethylsilsesquioxane (film former) | 5 |

Example 2

A skin protector with the following composition was made using the typical techniques used in the field of cosmetics:

| Compound Name (Composition 2) | Content (wt. %) |
|---|---|
| Octyloctanoate (oil component) | 50 |
| Propyleneglycol 2000 (glide agent) | 40 |
| Polymethacrylicacidisobutylester (film former) | 10 |

Characterization

Both compositions 1 and 2 were applied to the skin of the inner thighs of 10 female test persons of ages between 15 and 50. After the test persons swam for 20 minutes, the effectiveness was still at least 50% in both cases. Both compositions resulted only in at most 40% decrease of natural water loss through the skin (TEWL value as described above, transpiration) and thus did not seal the skin like other products in the prior art. The skin protectors according to the invention resulted in an improved protection of the skin by adhering and cross-linking the cells of the outer (dead) skin layer. This was a surprising effect of using film formers in skin protectors for the skin. The oil component allowed for high flexibility of the skin. The glide agents allowed for good glide effectiveness and therefore less excoriation of the skin.

Furthermore, skin elasticity was measured using a MPA580 Cutometer by lifting, stretching and releasing the skin. Peaks and troughs are measured to determine the flexibility of the skin. The skin protector as described in the examples above was applied to the skin and allowed to dry for 5 minutes. The difference to untreated skin was at most 0.02 mm in when the skin was lifted.

What is claimed is:

1. An oil-based skin protector for application to the human skin comprising at least one film former, an oil component, and water, wherein the film former comprises polymethylsilsesquioxane; wherein the skin protector is provided in the form of a liquid solution having a solid content of less than 0.1 wt. %; wherein the water content in the skin protector is less than 1 wt. %; wherein the skin protector provided in the form of a liquid solution has a viscosity in a range from 10 to 1000 mPa·s as measured at 20° C. and 1 atmosphere; and wherein a transepidermal water loss is at least 11 g/hm2 when 0.0036 g/cm2 of the skin protector is applied to the skin.

2. The skin protector according to claim 1, comprising the oil component in an amount from 45 to 70 wt. %.

3. The skin protector according to claim 2 wherein the oil component is selected from the group consisting of squalan, neutral oil, babassu oil, coconut oil, palm kernel oil, octyl octanoate, isopropyl palmitate, isopropyl myristate, cyclopentasiloxane, cyclohexasiloxane, C12-C18 alkyl benzoate, or dodecamethylcyclohexasiloxan.

4. The skin protector according to claim 1 wherein the film former is selected from the group consisting of polymethylsilsesquioxane, derivatives of polymethacrylic acid, polymethycrylic acid isobutylester, polymers comprising methylsilsesquioxy and trialkylsilylunits, trimethylsiloxysilicate, polypropylsilsesquioxane, acrylate copolymer, acrylates/acrylamide copolymer, butyl ester of PVM/MA copolymer (copolymer of methyl vinyl ether and maleic anhydride), carboxymethyl chitin, chitosan, hydroxypropyl cellulose, polyquaternium-36, PVP (polyvinylpyrrolidone), PVP/VA copolymer (polyvinylpyrrolidone/vinyl acetate), VA/crotonates copolymer (vinyl acetate/crotonic acid copolymer), vinyl caprolactam/PCP/dimethylaminoctyl methyacrylate copolymer, or mixtures thereof.

5. The skin protector according to claim 1 comprising the at least one film former in an amount from 3 to 15 wt. %.

6. The skin protector according to claim 1 further comprises at least one glide agent, wherein the glide agent is selected from the group consisting of polyalkylene glycol, dimethicone, dimethiconol, jojoba oil, *butyrospermum parii*, and rape seed oil.

7. The skin protector according to claim 6 wherein the glide agent is comprised in an amount from 15 to 52 wt. %.

8. The skin protector according to claim 1 for application to the human skin, wherein the human skin is selected from the group comprising of human skin on the feet, under the female breast, the upper arms, inner thighs, the shoulders and/or the back.

9. The skin protector according to claim 2, comprising the oil component in an amount from 50 to 65 wt. %.

10. The skin protector according to claim 5 comprising the at least one film former in an amount from 4 to 12 wt. %.

11. The skin protector according to claim 7 wherein the glide agent is comprised in an amount from 23 to 46 wt. %.

12. The skin protector according to claim 1 has viscosity in a range from 100 to 800 mPa·s.

13. The skin protector according to claim 1 is hydrophobic.

* * * * *

UNITED STATES PATENT AND TRADEMARK OFFICE
CERTIFICATE OF CORRECTION

PATENT NO. : 10,105,304 B2
APPLICATION NO. : 15/112983
DATED : October 23, 2018
INVENTOR(S) : Herbert Widulle It is certified that error appears in the above-identified patent and that said Letters Patent is hereby corrected as shown below:

On the Title Page

Page 2, Column 1, item [56], Line 8, under Other Publications, change "10.1111/06000536." to --10.1111/j.16000536.--.

Page 2, Column 2, item [56], Line 18, under Other Publications, change "Tospearl" to --Tospearl*--.

In the Specification

Column 2, Line 10, change "squalan," to --squalane,--.

Column 2, Line 15, change "dodecamethylcyclohexasiloxan." to --dodecamethylcyclohexasiloxane.--.

Column 2, Line 38, change "polymethycrylic" to --polymethacrylic--.

Column 2, Lines 39-40, change "trialkylsilylunits," to --trialkylsilyl units,--.

Column 2, Lines 47-48, change "dymethylaminoctyl" to --dimethylaminooctyl--.

Column 2, Line 48, change "methyacrylate" to --methacrylate--.

Column 2, Line 48, change "thereof" to --thereof.--.

Column 2, Line 57, change "parii," to --parkii,--.

Column 3, Line 41, change "90°" to --90° C.--.

In the Claims

Column 4, Line 55, Claim 1, change "g/hm2" to --g/hm$^2$--.

Signed and Sealed this
Ninth Day of July, 2019

Andrei Iancu
*Director of the United States Patent and Trademark Office*

CERTIFICATE OF CORRECTION (continued)
U.S. Pat. No. 10,105,304 B2

Column 4, Line 56, Claim 1, change "g/cm2" to --g/cm$^2$--.

Column 4, Line 61, Claim 3, change "squalan," to --squalane,--.

Column 4, Line 65, Claim 3, change "dodecamethylcyclohexasiloxan." to --dodecamethylcyclohexasiloxane.--.

Column 5, Line 2, Claim 4, change "polymethycrylic" to --polymethacrylic--.

Column 5, Line 3, Claim 4, change "trialkylsilylunits," to --trialkylsilyl units,--.

Column 5, Line 11, Claim 4, change "dimethylaminoctyl" to --dimethylaminooctyl--.

Column 5, Lines 11-12, Claim 4, change "methyacrylate" to --methacrylate--.

Column 5, Line 18, Claim 6, change "parii," to --parkii,--.